United States Patent [19]

Strope

[11] 4,036,904
[45] July 19, 1977

[54] ISOMERIZATION OF ALLENES IN A HYDROCARBON STREAM USING MAGNESIUM OXIDE CATALYST

[75] Inventor: Daniel J. Strope, Bartlesville, Okla.

[73] Assignee: Phillips Petroleum Company, Bartlesville, Okla.

[21] Appl. No.: 698,250

[22] Filed: June 21, 1976

[51] Int. Cl.$^2$ .................. C07C 7/00; C07C 11/12; C07C 11/14

[52] U.S. Cl. .................. 260/681.5 R; 260/677 A; 260/678; 260/680 R; 260/683 D

[58] Field of Search .................. 260/681.5, 677, 678, 260/680, 683 D

[56] References Cited

U.S. PATENT DOCUMENTS

| | | | |
|---|---|---|---|
| 2,353,552 | 7/1944 | Drennan | 260/683.2 |
| 2,361,613 | 10/1944 | Drennan | 260/683.2 |
| 2,548,619 | 4/1951 | Ray | 260/677 |
| 2,594,706 | 4/1952 | Allan | 260/678 |
| 3,340,317 | 9/1967 | Kenton | 260/666 |
| 3,369,054 | 2/1968 | Zellinski et al. | 260/678 |
| 3,449,463 | 6/1969 | Kenton et al. | 260/677 |
| 3,671,605 | 6/1972 | Smith | 260/678 |
| 3,707,579 | 12/1972 | Montgomery | 260/683 D |
| 3,745,195 | 7/1973 | Rothman et al. | 260/681.5 R |
| 3,865,751 | 2/1975 | Banks et al. | 260/666 A |

OTHER PUBLICATIONS

Reynold C. Fuson, Reactions of Organic Compounds, John Wiley and Sons, Inc., New York, 1962, p. 694.

*Primary Examiner*—Veronica O'Keefe

[57] ABSTRACT

The allenic impurities in a C-4 stream comprising 1,3-butadiene and at least one allenic impurity are reduced to nondetectable levels by contacting the stream with a magnesium oxide catalyst.

8 Claims, No Drawings

ISOMERIZATION OF ALLENES IN A HYDROCARBON STREAM USING MAGNESIUM OXIDE CATALYST

This invention relates to the isomerization of allenes.

A variety of hydrocarbon streams can be isolated from the effluent of a naphtha or gas oil cracker. This effluent can be separated by simple distillation into streams containing two carbon atoms (C-2 hydrocarbon streams) such as ethane and ethylene; streams containing C-3 hydrocarbons, such as propane and propylene; C-4 hydrocarbons, such as butane, butenes and butadiene; C-5 hydrocarbons, such as pentane, isoprene, isopetanes, pentenes and isopentenes; and so on.

These C-4 hydrocarbon streams generally contain about 20 to 40 percent 1,3-butadiene, with the remainder comprising other C-4 hydrocarbons, such as isobutane, n-butane, isobutylene, 1-butene and cis- and trans-2-butene.

Thus, to extract the butadiene values from a stream containing such a variety of C-4 hydrocarbons requires a sophisticated distillation process and/or an extractive distillation process using a selective solvent to absorb the butadiene values out of the mixture of C-4 hydrocarbons. Both of these processes are expensive, requiring a high capital investment and having a high energy requirement.

It has been proposed to recover the butadiene values in a commercial C-4 hydrocarbon stream from the stream by selectively cyclodimerizing the butadiene values to 4-vinylcyclohexene, then subjecting the mixture to simple flash distillation to separate the C-4 hydrocarbons from the cyclodimer. The separated 4-vinylcyclohexene can then be depolymerized to form 1,3-butadiene, or it can be used as an intermediate for further synthesis reactions, such as for conversion to 4-vinylcyclohexene-1,2-epoxide, which can be used for producting polymeric materials.

It is known that 1,3-butadiene can be cyclodimerized by thermal, noncatalytic techniques. However, these techniques require a high temperature and dimerization is slow. Additionally, a simultaneous polymerization occurs and competes with the desired reaction.

It is also known to catalytically cyclodimerize 1,3-butadiene. Utilization of catalysts has been recommended to improve the rate of butadiene dimerization. A variety of catalysts are known for cyclodimerizing 1,3-butadiene to (1) a non-specific mixture of 4-vinylcyclohexene and 1,5-cyclooctadiene, (2) 4-vinylcyclohexene in a specific manner, and (3) 1,5-cyclooctadiene in a specific manner. The 1,5-cyclooctadiene can be isomerized to 4-vinylcyclohexene.

Catalysts for cyclodimerizing butadiene are generally constituted by such metals as iron, ruthenium, nickel and cobalt, which include one or more ligands, such as, for example, a nitrosyl ligand in association with another ligand, such as a carbonyl ligand and/or a pi-allyl ligand. While these catalysts and catalyst systems are effective in promoting the cyclodimerization of butadiene, many are moisture-sensitive and many, if not all, are air-sensitive. These are, however, problems which are easily solved, merely by maintaining an inert atmosphere in and around the catalyst.

It has been found that these cyclodimerization catalysts are "poisoned" by allene and allenic compounds, such as 1,2-butadiene. In large-scale operations, small amounts of these impurities in the feedstream can appreciably shorten the life of the catalyst. Since such impurities may be present in such small quantities that ordinary treatment, such as fractional distillation, to remove them may not be feasible, other methods may be required to reduce the amount of such impurities to acceptable levels. Preferably, these impurities are reduced to such a level that they cannot be detected by presently available analytical procedures.

Therefore, it is an object of this invention to provide a process to reduce the amount of allenic compounds in a C-4 stream.

Other objects, aspects and advantages of the present invention will be apparent to those skilled in the art from a reading of the following disclosure and the appended claims.

In accordance with the present invention there is provided a process for reducing the amount of allenic compounds in a C-4 feedstream, which comprises contacting such C-4 stream with magnesium oxide, whereby allenic impurities in such stream are converted to compounds which do not adversely affect the catalyst or catalyst system subsequently employed.

More specifically, the allenic impurities which are converted according to the present invention include: allene, which has the formula $$CH_2 = C = CH_2,$$

1,2-butadiene, which has the formula $$CH_2 = C = CH - CH_3, \text{ and}$$

higher allenes. These impurities can broadly be represented by the formula

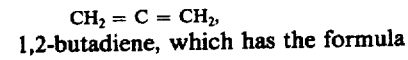

where R is hydrogen or an alkyl group having 1 to 4 carbon atoms.

The allenic impurities are removed by converting them to acetylenic compounds or to isomeric dienes by passing the stream containing these impurities over a magnesium oxide catalyst at a temperature of about 85° to 355° C, preferably 275 to 355° C, at a rate of about 10 to 500, preferably about 20 to 200 volumes of gas per volume of catalyst per hour. Thus allene is thereby converted to methyl acetylene; 1,2-butadiene is thereby converted to 2-butyne or 1,3-butadiene; and so on.

The catalyst of this invention is magnesium oxide. In one embodiment, the magnesium oxide can be obtained by heating a compound containing magnesium, such as magnesium hydroxide, which decomposes to produce magnesium oxide. Minor amounts of other materials, such as silicon oxide or aluminum oxide, can be present as impurities without departing from the scope of the invention. Depending upon the contacting technique to be used in this invention, the magnesium oxide can be in the form of pellets, extrudates, or fine powder. The magnesium oxide is activated by heating in air, preferably in a stream of flowing air, from 1 to 30 hours at a temperature of 400° to 1200° C, preferably about 750° to 1100° C.

The method of this invention for converting allenic impurities to innocuous products is useful for treating the feedstream of any catalytic process wherein the catalyst therein employed is poisoned by such allenes. The method of this invention is particularly useful for treating the feedstream of a catalytic cyclodimerization process for cyclodimerizing conjugated dienes having from 4 to 8 carbon atoms per molecule. Some specific examples of these are: 1,3-butadiene, isoprene, piperylene, 2,3-dimethyl-1,3-butadiene, 1,3-hexadiene, 2,4-octadiene, 2-methyl-1,3-pentadiene, and the like.

These conjugated dienes are contacted with a cyclodimerization catalyst under suitable reaction conditions to effect cyclodimerization of the conjugated diene. While it is contemplated that any cyclodimerization process can be used, the method of this invention is particularly applicable to cyclodimerization processes employing a dinitrosyl iron complex catalyst, such as those disclosed in U.S. Pat. Nos. 3,377,397 and 3,510,533, both of which are incorporated herein by reference.

The conjugated diene is contacted with a cyclodimerization catalyst at a temperature in the range of about 0° to about 100° C. The contact can be carried out either batchwise or continuously using any conventional contacting apparatus. The contact time will vary according to the efficiency of the contacting technique, the reaction temperature, and the desired degree of conversion, but will generally be in the range of from about 1 minute to about 10 hours. The catalyst usage will be in the range of from about 0.001 to 10, preferably 0.01 to 1 millimole of iron per mole of conjugated diene. The dimerization can be carried out at any convenient pressure which is sufficient to maintain a substantially liquid state.

At the completion of te cyclodimerization reaction, the dimeric products are recovered by any conventional technique such as by fractionation, crystallization, absorption and the like.

The recovered cyclodimer product can be converted to its conjugated diene precursor by techniques known in the art, such as by pyrolysis.

The following examples illustrate the invention:

EXAMPLE I

A sample of a C-4 hydrocarbon stream was analyzed by gas chromatography. The main constituents of the C-4 stream, including the allenic impurities, are given in the table below. A portion of this C-4 stream was passed through a ½-inch diameter × 20-inch long stainless steel, cylindrical reactor containing 50 ml of magnesium oxide catalyst supported between glass beads. The tube reactor was heated by external resistance elements. The temperature of the catalyst bed was maintained at 90° C and the flow rate of the C-4 stream through the catalyst bed was about 120 ml/minute (GHSV about 144 v/v/hr.). The initial and final GLC analyses are given below:

Table I

| Constituent | Relative Concentration, % | |
|---|---|---|
| | Before Treatment | After Treatment |
| Isobutane | 1.59 | * |
| n-Butane | 7.86 | * |
| Neopentane | 0.22 | * |
| Butene-2 and isobutene | 39.89 | * |
| Trans-butene-2 | 5.79 | * |
| Cis-butene-2 | 5.88 | * |
| 1,3-Butadiene | 35.36 | 37.6 |
| Allene | 0.33 | None Detected |
| 1,2-Butadiene | 0.29 | None Detected |
| 1-Butyne | 0.16 | * |

Table I-continued

| Constituent | Relative Concentration, % | |
|---|---|---|
| | Before Treatment | After Treatment |
| 2-Butyne | 0.002 | 0.147 |

*No change.

The above data demonstrate that both allene and 1,2-butadiene were reduced to nondetectable levels, while the levels of 1,3-butadiene and 2-butyne, the isomerization products of 1,2-butadiene, increased.

EXAMPLE II

Additional portions of the above-described C-4 hydrocarbon stream were passed through the catalyst bed employed in Example I, at a GHSV of 30 and the temperatures indicated below:

Table II

| Temp. | Constituent | Relative Concentration, % | |
|---|---|---|---|
| | | Before Treatment | After Treatment |
| 295° C | 1,3-Butadiene | 36.274 | 34.716 |
| | Allene | 0.070 | None Detected |
| | 1,2-Butadiene | 0.192 | None Detected |
| 335° C | 1,3-Butadiene | 36.04 | 34.998 |
| | Allene | 0.128 | None Detected |
| | 1,2-Butadiene | 0.240 | None Detected |

The above data demonstrate that the isomerization of allene and 1,2-butadiene can be carried out over a wide temperature range.

Reasonable variations and modifications, which will be apparent to those skilled in the art, can be made in this invention without departing from the spirit and scope thereof.

What is claimed is:

1. A process for reducing the amount of allenic impurities in a C-4 stream comprising 1,3-butadiene and at least one allenic impurity which consists of contacting said stream with a catalyst consisting of magnesium oxide at a temperature in the approximate range of 85° to 355° C.

2. The process of claim 1 wherein said stream is contacted with said catalyst at a temperature in the approximate range of 275° to 355° C.

3. The process of claim 1 wherein said impurity is allene.

4. The process of claim 1 wherein said impurity is 1,2-butadiene.

5. In a process for cyclodimerizing 1,3-butadiene by contacting a C₄ stream comprising 1,3-butadiene, and at least one allenic impurity with a cyclodimerization catalyst and thereafter recovering at least one cyclodimer of 1,3-butadiene from the thus-contacted stream, the improvement which consists of contacting said stream with an isomerization catalyst consisting of magnesium oxide prior to contacting said stream with said cyclodimerization catalyst thereby isomerizing said allenic impurity.

6. The process of claim 5 wherein said C-4 stream is contacted with said magnesium oxide catalyst at a temperature in the approximate range of 85° to 355° C.

7. The process of claim 5 wherein said impurity is allene.

8. The process of claim 5 wherein said impurity is 1,2-butadiene.

* * * * *